United States Patent [19]

Prud'homme et al.

[11] Patent Number: 4,629,566

[45] Date of Patent: * Dec. 16, 1986

[54] METHOD FOR CHARACTERIZING THE MOLECULAR WEIGHT AND MOLECULAR WEIGHT DISTRIBUTION OF ULTRA-HIGH MOLECULAR WEIGHT WATER SOLUBLE POLYMERS

[75] Inventors: Robert K. Prud'homme, Trenton, N.J.; Frederick W. Stanley, Jr.; Martin W. Langhorst, both of Midland, Mich.

[73] Assignee: The Dow Chemical Company, Midland, Mich.

[*] Notice: The portion of the term of this patent subsequent to Jul. 30, 2002 has been disclaimed.

[21] Appl. No.: 738,204

[22] Filed: May 24, 1985

Related U.S. Application Data

[63] Continuation of Ser. No. 523,818, Aug. 15, 1983, Pat. No. 4,532,043.

[51] Int. Cl.$^4$ ............................................. B01D 15/08
[52] U.S. Cl. .................................... 110/635; 210/656; 422/70
[58] Field of Search .................. 210/635, 656; 422/70

[56] References Cited

U.S. PATENT DOCUMENTS

| | | | |
|---|---|---|---|
| 3,002,823 | 10/1961 | Flodin et al. | 210/635 |
| 3,059,524 | 10/1962 | Grassmann | 210/656 |
| 3,298,925 | 1/1967 | Mosback | 210/635 |
| 3,326,875 | 6/1967 | Moore et al. | 210/656 |
| 3,694,149 | 9/1972 | Matsumoto | 210/635 |
| 3,865,717 | 2/1975 | Small | 209/1 |
| 3,962,206 | 6/1976 | Butler | 210/635 |
| 4,280,923 | 7/1981 | Small et al. | 209/1 |

OTHER PUBLICATIONS

"Molecular Size Determination of Xanthan Polysaccharide", by Prud'homme et al. Carbohydrate Research, 106, (1982), pp. 225-233.
"Separations of High Molecular Weight Water Soluble Polymers by Means of Hydrodynamic Chromatography," by K. A. Larson, Department of Chemical Eng., Princeton University, (1983).
"Hydrodynamic Chromatography", by Small et al., Anal. Chem., 54, 892A, (1982).
"Use of Isocyanides for the Immobilization of Biological Molecules", by Vretblad et al. in Acta Chem., Scand. 27, No. 8, 2769-2780, (1973).
"Elution Volume Measurement in Size Exclusion Chromatography", by Chamberlin et al. in Anal. Chem. 55, 428-432, (1983).
"Development and Application of an Integrated, High Speed, Computerized Hydrodynamic Chromatograph", by McGowan et al. Journal of Colloid and Interface Science, vol. 1, No. 1, Sept., 94-106, (1982).
"Molecular Weight of Xanthan Polysaccharide", by Holzwarth Carbohydrate Research, 66, 173-186, (1978).
"Orientation of Rigid Macromolecules During Hydrodynamic Chromatography Separations", by Prud'homme et al., Separation Science Tech., 18, (2), 121-134, (1983).

(List continued on next page.)

*Primary Examiner*—John Adee
*Attorney, Agent, or Firm*—Burke M. Holldorson

[57] ABSTRACT

The molecular weight and molecular weight distribution of diverse ultra-high molecular weight water soluble polymers is rapidly determined based on apparent size by passage of extremely dilute samples of the polymer (1–250 ppm) through a column of nonporous packing whereby separation into molecular weight (apparent size) fractions is obtained predominantly based on flow (i.e., hydrodynamic chromatography). Detection of the extremely dilute sample polymer is accomplished, e.g., by tagging the polymer with a fluorescent agent and using a flow-through fluorometer detector. The molecular weight characterization of the polymers is determined independent or less dependent of the composition of the polymer by analyzing the sample in its nonionized form.

6 Claims, 4 Drawing Figures

OTHER PUBLICATIONS

"Separation Mechanisms in Gel Permeation Chromatography", by W. W. Yau, C. P. Malone, and H. L. Suchan, Separ. Science 5, 259, (1970).

"Exclusion Chromatography", by K. O. Pedersen, Archives of Biochemistry and Biophysics, Supplement 1, 157–168, (1962).

"Extraparticle Diffusion, Effects in Gel Permeation Chromatography II. Experimental Results", by A. Ouano and J. A. Bisenberger, Appl. Polymer Science, 14, 483, (1970).

"Separation by Flow", by E. A. DiMarzio and C. M. Guttman, Macromolecules, 3, 131, (1970).

"Gel Permeation Chromatography: On the Mechanism of Separation by Flow", by S. Mori, R. S. Porter and J. F. Johnson, Analytical Chem., 46, No. 11, 1599, Sept. (1974).

Typical Chromatogram

42 cm x 10 mm I.D. column packed with 15 micrometer cation exchange resin
Flow rate = 0.5 ml/min.
0.1 M $NaH_2PO_4$, pH 4
0.1% Brij

Typical Molecular Weight Distribution

Average Molecular Weights
$M_n$ = 375,000
$M_w$ = 4,430,000
$M_z$ = 7,950,000

METHOD FOR CHARACTERIZING THE MOLECULAR WEIGHT AND MOLECULAR WEIGHT DISTRIBUTION OF ULTRA-HIGH MOLECULAR WEIGHT WATER SOLUBLE POLYMERS

CROSS-REFERENCE TO RELATED APPLICATION

This application is a continuation of related copending application Ser. No. 523,818, filed Aug. 15, 1983, now U.S. Pat. No. 4,532,043.

BACKGROUND OF THE INVENTION

Ultra-high molecular weight, water soluble synthetic and natural polymers are used in a variety of important industrial and other applications. Better knowledge of the molecular weight distribution of these polymers could contribute significantly to their design and also provide a better understanding of their behavior in given applications. There have been numerous attempts to characterize the molecular weight distribution of these polymers by conventional size exclusion chromatography (SEC). The principal shortcomings associated with the application of this analytical technique to these polymers are poor resolution of ultra-high molecular weight polymers and poor detector response. Column packing materials generally have an exclusion limit of $\sim 2\overline{M}$. That is, SEC can generally be used to size molecules $>2\overline{M}$. The molecular weight distribution of important water soluble polymers can range up to $\geq 30\overline{M}$ based on sedimentation experiments. Application of SEC methods provides little if any meaningful information about these ultra-high molecular weight materials with molecular weights $>2\overline{M}$.

Due to the limitations of SEC methods, other techniques have been investigated for characterizing ultra-high molecular weight polymers. Holzwarth (Carb. Res., 66, 173-186, 1978) described ultracentrifugation experiments using fluorescence detection to characterize xanthan polysaccharide polymers. These experiments require the use of highly complex apparatus which is not generally suitable for routine analysis work. In addition, despite the report of encouraging results, the technique has not found wide acceptance.

Theoretically, light scattering experiments would be extendable to these characterizations of molecular weight. However, in practice, this method has experimental constraints which can produce unreliable data due to alteration of the sample by necessary sample preparation. In addition, no distribution information is available from this method of analysis.

Yet another approach to developing methods for characterizing these polymers has been the method of hydrodynamic chromatography first developed by Small for sizing colloidal particles (U.S. Pat. No. 3,865,717) and later extended in a modified fashion to the field of water soluble polymers, such as dissolved sodium polystyrene sulfonate fractions (U.S. Pat. No. 4,280,923). In contrast to conventional SEC methods where separation occurs by diffusion into the pores of a porous packing material, HDC separations occur and are due to flow through the interstitial spaces of a porous bed of nonporous packing material. Small's attempt to use this method to characterize water soluble polymers by molecular weight was only partially successful. That is, in none of the work described by Small is the method extended beyond the conventional limits of SEC. Hence, both HDC and SEC as heretofore developed have not been successfully used to characterize high molecular weight polymers of greater than 2 million molecular weight.

TERMS

"Ultra-high molecular weight polymers" mean polymers having a weight average molecular weight of greater than $1\overline{M}$ molecular weight as determined by light scattering methods.

"Flow chromatography" (hydrodynamic chromatography) means a method of chromatography where minimized or no retardation is imparted by interaction between the chromatographic packing and sample and in contrast separation is predominantly by flow through interstitial spaces of a porous bed composed of a nonporous packing. "Flow chromatography" is demonstrated and observed by the condition of the progression of the sample species through the column faster than the mobile phase through the column.

"Water soluble" means and is limited to polymers which are capable of being dissolved in water to form a homogeneous (single phase) solution.

"Polymer" means and includes synthetic and naturally occurring polymers.

"Polyelectrolyte" means and includes nonionic water soluble polymers which are derivatized to polyelectrolytes for purpose of the molecular weight characterizations using the invention as well as all cationic and anionic water soluble polymers.

"Detectable limit" means the concentration in solution of an injected polymer sample which upon its elution produces a signal of not less than 2.5 times noise.

"Apparent size" means and refers to the elution position of a polymer species in flow chromatography relative to that for the mobile phase as determined by any accurate measurement technique.

"Upper limit" and "sample volume" means in reference to the maximum concentration and volume of the injected polymer sample, that concentration and volume, respectively, above which the elution time of the sample peak becomes a function of sample viscosity and not a function of apparent size only.

"Molecular weight" means the calculated average molecular weight or molecular weight range for a polymer or polymer fraction wherein the calculations are based on apparent size.

"Molecular weight distribution" means a tabulation of molecular weight fractions and their relative amounts as calculated based on apparent size.

"Aqueous eluent" means any water containing solvent for dissolving water soluble polymers and which is otherwise suitable for the purposes of the invention.

THE INVENTION

The invention is a new liquid chromatographic method for characterizing ultra-high molecular weight, water soluble polymers according to molecular weight distribution. The technique is particularly of value in characterizing polymers with weight average molecular weights ($\overline{M}_w$) of greater than $\sim 2\overline{M}$ (or in the range above that possible by prior liquid chromatographic methods such as SEC and HDC).

Specifically the invention is an improved liquid chromatographic method for characterizing water soluble polymers by molecular weight and molecular weight distribution based on apparent size which comprises:

(a) adding to an aqueous eluent a sample of a detectable polymer in a solution concentration between the detectable limit and an upper limit below the concentration at which the elution of the polymer is detrimentally influenced by concentration, the sample added being dissolved in a primarily aqueous diluent not incompatible with the eluent, the added sample volume being not greater than that volume which would detrimentally influence the chromatography;

(b) passing the combined eluent and sample at a low flow rate which does not influence the elution position of the sample through a porous body composed of a packed bed of impenetrable particles whereby the apparent size fractions of the polymer sample are separated by flow chromatography;

(c) detecting the amount of the eluting apparent size fractions of the polymer species; and (d) using the data of step (c) to characterize the molecular weight and molecular weight distribution of the detected water soluble polymer.

The invention as set out above typically requires the addition of samples of from about 1 to about 250 parts per million (ppm) concentration in aqueous diluent (preferably eluent); coupled with the injection of from 1 to 100 μl of sample volume. These extremely dilute polymer concentrations and small sample volumes result in the addition of from <0.01 μg to 10 μg of sample polymer for the purposes of the liquid chromatographic separation and apparent size determination according to the invention. These small polymer sample amounts are generally nondetectable or inadequately detectable by conventional liquid chroma tography detectors developed for past SEC and HDC methods.

In order to remain within the sample and detector parameters of the invention, therefore, many of the polymer samples analyzed by the invention are advantageously derivatized to forms in which extremely dilute sample concentrations may be sensitively detected by usual liquid chromatography detectors. This key step of the invention preferably uses fluorescent labeling to enhance detectability of the polymer sample. In this reaction, e.g., a primary fluorescent amine is coupled to the carboxyl moieties present in the polymer sample or made present by a prior reaction such as hydrolysis of an amide group on the polymer backbone. By this technique, essentially all important water soluble polymers can be characterized by the practice of the invention. Included among these are ultra-high molecular weight polymers of polyacrylamide and hydrolyzed polymers thereof, copolymers of acrylamide and acrylic acid, polyacrylic acid, methacrylic acid and its water soluble copolymers, polymers containing methacrylate and acrylate esters, ethyl and methyl acrylates, cationic acrylates and water soluble cellulosics such as carboxy methyl cellulose.

The above list of polymers is illustrative and not comprehensive of the diverse water soluble polymers which can be characterized by molecular weight using the invention. In addition, other methods of derivatization which would produce detectable polymer for the purposes of the invention can be substituted for fluorescent labeling with anticipated satisfactory results.

Another key aspect of the invention is the practice of controlling apparent size of the polymer molecules independent of composition. This involves preparation of sample and eluent solutions under carefully controlled pH parameters designed to convert (or maintain) the polymer polyelectrolyte as a relatively nonionic species. The pH used to effect this condition is numerically equivalent to the pKa of the corresponding acid of the polymer molecule. For example, a pH within the carefully controlled range of from 3.8 to 4.0 is beneficially practiced with respect to acrylamide/acrylic acid based copolymers. In this range apparent size of the copolymer molecules is relatively composition independent and, hence, more reliably a function of the actual molecular weight of the polymer molecules.

In addition to pH control, the eluent may necessarily require a surfactant to mask any possible retardation sites or other chromatography effecting sites within the column, and an electrolyte to level the viscosity of the polymer containing solution being analyzed. Ideally, the viscosity of the sample solution and that of the eluent should not be so different as to detrimentally influence the elution of the polymer sample. In this regard diluents selected for the sample solution are compatible with the eluent to the extent that these viscosity parameters are substantially met. This is best met by using an aqueous diluent of the same composition as the eluent.

The various nonporous or impenetrable packing materials which can be used in the new method described herein can be equivalent to those packings previously used in colloid analysis methods by hydrodynamic chromatography as described for example by McGowan and Langhorst, J. Colloid & Int. Sci., 89, 94 (1982) and Small and Langhorst, Anal. Chem., 54 892A (1982). The above-cited teachings are both fully incorporated in this disclosure by reference.

THE DRAWING

Yet further details, facets and applications of the invented method are made apparent by reference to the following more detailed description of the invention taken together with the accompanying drawings wherein.

DETAILED DESCRIPTION OF THE INVENTION

Apparatus

Figure 1:
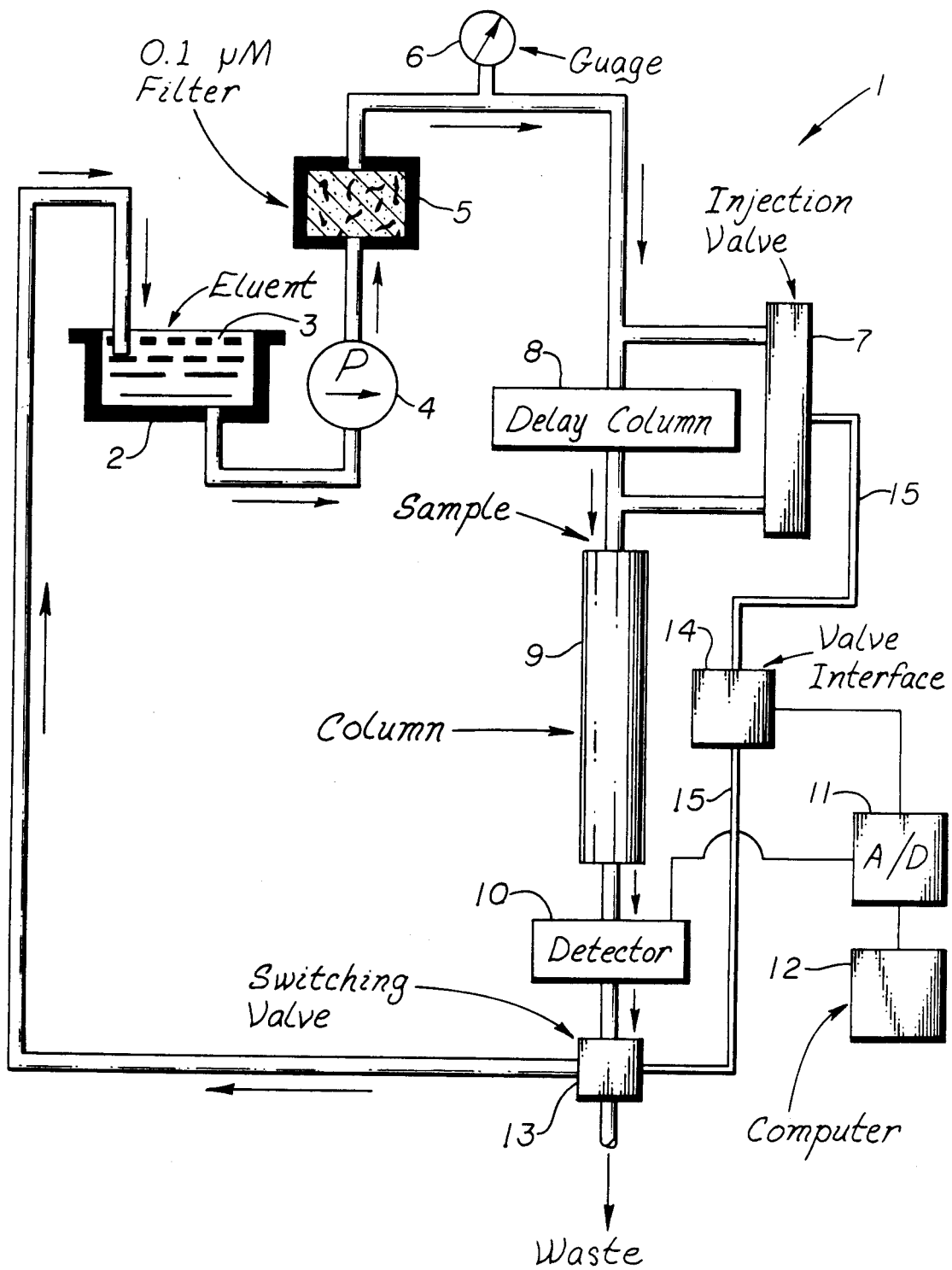
FIG. 1 is an elevational view of a preferred form of a liquid chromatographic apparatus for practicing the method of this invention.

The chromatographic apparatus illustrated in FIG. 1 is assembled from commercially available components. The apparatus designated generally by reference 1 comprises an eluent reservoir 2 from which an aqueous eluent based solution 3 is withdrawn by a chromatographic pump 4 (suitably a Waters M-45 or other pump which provides preferably pulseless pumping of the eluent).

The pump 4 is followed by an in-line filter 5 (e.g., having a nominal porosity of, e.g., 0.1 micrometer) and pressure gauge 6 through which the eluent solution is successively passed to an injection valve 7. The preferred injection valve is a 12-port valve to accommodate the precise simultaneous injection of sample solution and a marker solution.

Interposed between points of separated injection of the marker solution and sample solution is a delay column 8 which delays the marker, e.g., 10-20 seconds relative to the sample solution. The sample solution in this scheme is bypassed about the delay column and injected directly into a separating column designated 9. The separating column contains a porous bed of stationary phase composed of packed nonporous particles, preferably spheres suitably of a type heretofore developed for the flow separation of colloids. The delay column, while having no chromatography separation functionality, is desirably composed of a similar porous bed as used in the separating column 9. Other suitable methods for precisely determining the elution volume of sample polymer can, of course, be substituted for the marker and delay column scheme. For example, the precision flow metering device described by Chamberlin and Tuinstra, (Anal. Chem, 1983, 55, 428-432) and which is also the subject of U.S. patent application Ser. No. 280,668, filed July 6, 1981 by Miller and Small, would be an example of a precision flow meter envisioned herein for replacing the delayed marker method for determining precise elution volume of eluting polymer samples.

The column 9 is connected to a suitable flow through chromatography detector 10 of any suitable type for determining the extremely minute sample amounts eluting from column 9 in the practice of the invention. With respect to the fluorescence tagging method previously described, a suitable and preferred detector is a Perkin-Elmer Model 650-S Fluorescence Detector used with a flow cell attachment also supplied by Perkin-Elmer to modify the detector for flow analysis. The output of detector 10 is monitored by a suitable analog/digital converter 11, suitably a Model 760 Nelson Analytical A/D converter which can be successfully used to digitize the chromatographic data. A computer 12 calculates molecular weight and molecular weight distribution based on the digitized output of A/D converter 11. The computer is suitably a Hewlett Packard HP-85 with I/O ROM, Matrix ROM, ROM Drawer, and 16K Memory module provides the necessary data reduction tasks. Optionally, a disc drive and mass storage ROM can be used to store both programs and data files (chromatograms) rather than the magnetic tape, which is standard on the HP-85.

The injection valve 7 is pneumatically activated by a digital valve interface 14 connected to the injection valve by pneumatic line 15. The injection valve 7 and digital valve interface 14 are items which can be obtained from Valco Instrument Co., Inc., Houston, Tex. The digital valve interface 14 is activated by computer 12 through the A/D converter. The injection valve is manually loaded via syringe and the computer, by manual activation, causes the injection of the sample and marker simultaneously, and controls thereafter all sequences of the apparatus 1. A switching valve 13 receives the effluent from the detector 10 and by the control of the computer either returns the eluent to the reservoir or to waste.

Columns

The column resin packing used in the following experiments is a nonporous cation exchange resin or copolymer of 15 micron nominal diameter available commercially from Benson Company, Reno, Nev. The column packing resin can be sized using a HIAC particle size analyzer. The tubing into which the resin is packed is ⅛ inch O.D., 10 mm I.D. stainless steel tubing of 42 cm or 25 cm in length, which is available from Valco instrument Co., Inc., Houston, Tex. Column end fittings are obtained from Valco Instruments and 2-$\mu$m frits for end fittings are obtained from Beckman-Altex.

Columns are packed with the cation-exchange resin using a Haskel constant-pressure, air-driven, 2 h.p. pump, available from Haskel Engineering and Supply Co., Burbank, Calif.

Reagents

The eluent used contains as a suitable viscosity leveler from about 0.1 molar to 0.5 molar $NaH_2PO_4$ and as a suitable surfactant from about 0.01 to 0.1 percent (w/v) Brij or, alternatively, Triton X-100. The pH is adjusted according to the parameters described previously. For acrylamide/acrylic acid based sample polymers as a specific example, the pH is suitably controlled by the addition of $H_3PO_4$ to the eluent and sample solutions to control the pH between 3.8 and 4.0 as determined by a laboratory pH meter. The chemicals which are used in the following examples for the fluorescent tagging reaction are dimethylsulfoxide (DMSO) (available from Burdick & Jackson, Muskegon, MI), acetaldehyde, cyclohexylisocyanide and 5-amino fluorescein (all available from Aldrich Chemicals, Milwaukee, Wis.). Water soluble polyacrylamide standards can be obtained from Polysciences, Inc., Warrington, PA.

EXAMPLE 1

Preferred Fluorescent Tagging Procedure

To enhance the detectability of the polymer sample, the carboxyl functionality on the polymer backbone is tagged with a fluorescent compound. This reaction couples the carboxyl moiety with a fluorescent primary amine through a cyanide linkage to form a stable amide. Originally investigated for use on selected biologically oriented molecules (Acta Chemica Scand 27, 2679 (1973)), this reaction was recently applied to xanthan polysaccharides (Holzwarth, Ibid), and even more recently to polyacrylamides. These previous investigators have indicated that the level of tagging is ~1 percent by weight from spectroscopic measurements.

Specifically, in this example, polyacrylamide/polyacrylic acid copolymers are tagged following the procedure of Holzwarth (Ibid) with slight modifications. Twenty-five mls of 0.1 molar NaCl solution containing 0.5 percent (w/v) polymer and 25 mls of ½ $DMSO/H_2O$ are combined. The pH of this solution is adjusted to pH 7 if necessary. One hundred $\mu$l of acetaldehyde, 100 $\mu$l of cyclohexylisocyanide and 3 ml of a 1 mg/ml 5-amino fluorescein solution in DMSO are added. The reaction mixture is gently agitated to thoroughly mix the contents of the bottle, and then allowed to stand for at least 3 hours. Then, 1 ml of the reaction mixture is added to 10 ml of acetone, and shaken to precipitate the polymer. The vial is centrifuged for ~5 minutes at 1500 rpm, the liquid phase is decanted and replaced with 20 ml of eluent used for the analysis. The polymer is usually allowed to dissolve overnight before analysis.

Example 2

Calibration

This example describes the calibration procedure used to calibrate each chromatography column 9 for use in the apparatus 1. In the terminology below, $R_f$ means the ratio of the marker elution volume (time) to the sample solution volume (time). It is assumed that the flow rate during the experiment is relatively constant. Because ultra-high molecular weight (MW) polymer standards are not readily available, column 9 may be calibrated out of necessity using well characterized standards having less than 1$\overline{M}$ molecular weights. For example, column 9 may be calibrated using commercially available polyacrylamide standards ranging from 74,000 molecular weight to 2$\overline{M}$ molecular weight. The polyacrylamide standards must be hydrolyzed to accept the fluorescent labeling prior to analysis. The described delayed marker injection technique is employed during the calibration procedure, using the 74,000 molecular weight standard as the delayed marker.

Table I indicates that an increase in $R_f$ with increasing molecular weight is observed for the indicated series of polyacrylamide (PAAm) standards.

TABLE I

| | PAAm | |
|---|---|---|
| Rf | | MW |
| 1.0583 | | 270K |
| 1.0659 | | 500K |
| 1.0710 | | 1$\overline{M}$ |
| 1.0800 | | 2$\overline{M}$ |

Figure 2:
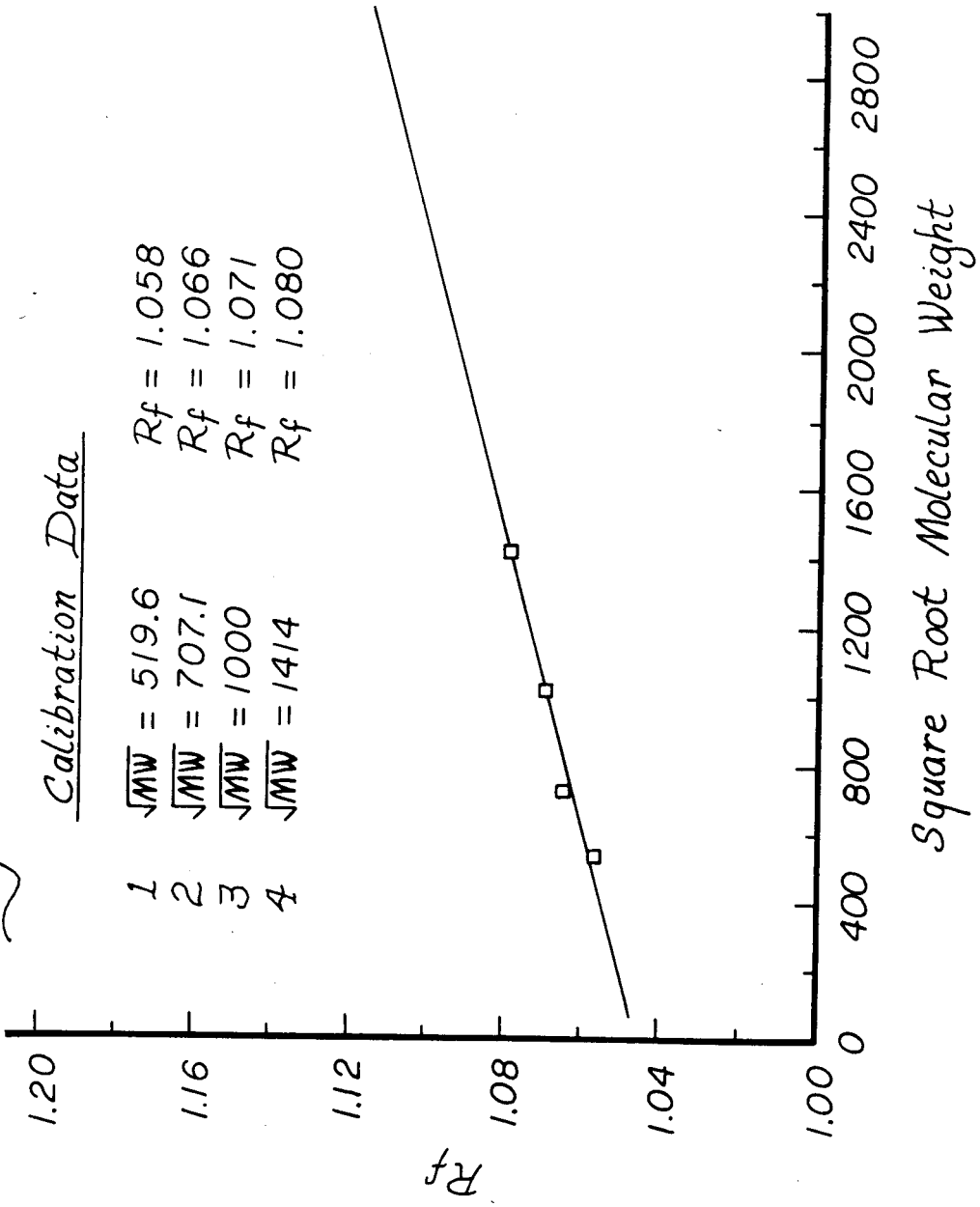
FIG. 2 is a typical calibration relationship (in graph form) developed using commercially available standards.

Several calibration relationships were evaluated from Table I including $R_f$ vs MW. This relationship is approximately linear, as illustrated in FIG. 2 for this PAAm series. While approximate linearity is observed, it is also apparent that important relative information from this analysis method can also be obtained from the polymers being investigated without calibrating the apparatus.

EXAMPLE 3

Calculations

The software for the described apparatus 1 was developed and applied using the following format illustrated below in block form.

| Data Entry into Array | Smoothing | Background Subtraction |
|---|---|---|
| MW Calculations | | Marker Peak Subtraction |
| Data Output | | |

The manner in which the data is smoothed, background subtracted and the marker peak identified and subtracted from the chromatogram is essentially identical to those subroutines originally developed for HDC analysis of latex (McGowan & Langhorst, (Ibid)). Using the previously developed calibration relationship for the column, the molecular weight is established for each of the data points taken during the experiment. The signal intensity and the molecular weight of that point are then used to calculate the average molecular weights and molecular weight distribution using the following relationships:

$Ri$ = height of response $Mi$ = MW of point $$\overline{M}_n = \frac{\Sigma Ri}{\Sigma \left(\frac{Ri}{Mi}\right)}$$

$$\overline{M}_w = \frac{\Sigma(RiMi)}{\Sigma Ri}$$

$$\overline{M}_z = \frac{\Sigma(RiMi^2)}{\Sigma(RiMi)}$$

Weight Fraction $= \frac{Ri}{\Sigma Ri} \times Mi \times \frac{\Delta T}{\Delta M}$ The above relationships are the same as those used in SEC and were used here without modification. (See, W. W. Yau, J. J. Kirkland, and D. D. Bly, "Modern Size Exclusion Chromatography," John Wiley and Sons (1979), incorporated fully by reference. The calculation step (i.e., step (d) of claim 1) may broadly be practiced using any scientifically accepted expression to calculate molecular weight and molecular weight distribution from the developed chromatographic data.

Figure 3:
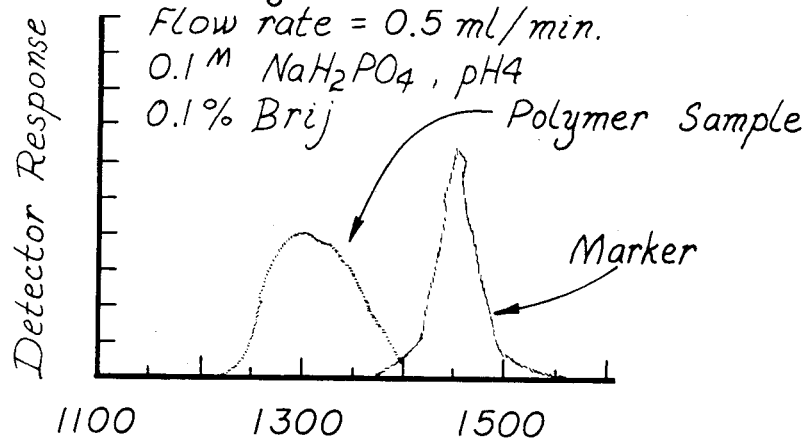
FIG. 3 is a reproduced typical chromatogram developed using the method of this invention for a water soluble polymer sample.
Figure 4:
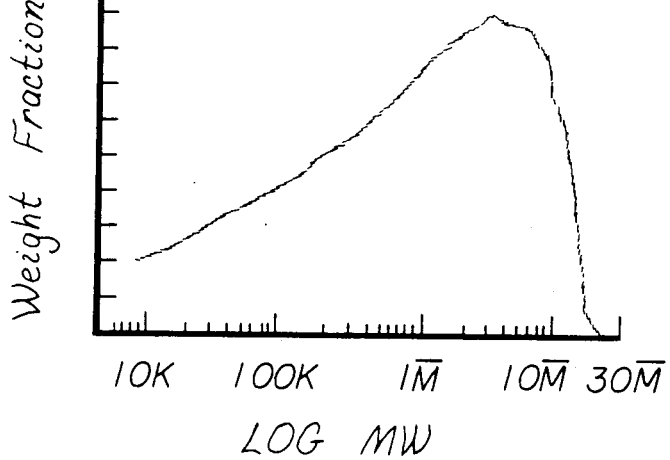
FIG. 4 is a typical molecular weight distribution (in graph form) developed using the invention.

FIGS. 3 and 4 illustrate a typical output. The sample analyzed in this instance is a copolymer of acrylamide and acrcylic acid. Using a previously determined calibration relationship and appropriate calculations such as previously described, the molecular weight distribution illustrated in FIG. 4 is calculated from the chromatogram, which is illustrated in FIG. 3. Also calculated are the average molecular weights based on number ($\overline{M}n$) and weight ($\overline{M}w$) and "Z" average.

EXAMPLE 4

Chromatography of Ultra-High Molecular Weight Polymers

Various chromatography parameters are investigated in this example. For the polyacrylamide samples investigated, too much Brij surfactant can be detrimental. For example, an increase in surfactant concentration from 0.1 to 0.4 percent (w/v) in 0.1 molar $NaH_2PO_4$ at pH 4 was observed to result in a decrease in $R_f$ for the polymer sample analyzed and a nondesirable increase in peak tailing. Similar behavior was observed when the ionic strength of the eluent was decreased from 0.1 molar to 0.002 molar. This behavior is believed due to a significant interaction between packing material, polymer and surfactant, which is not observed at a lower surfactant concentration. However, the detrimental influence of high surfactant concentration was not observed at 0.5 molar electrolyte concentration in the eluent in studies of polyacrylamide/acrylic acid polymer samples.

The flow rate can also influence the elution position of ultra-high molecular weight polymers. But, the dependence of elution position on flow rates was not as great at 0.5 molar electrolyte eluent concentration as that observed at 0.1 molar electrolyte eluent concentration for studied polyacrylamide/acrylic acid polymer samples. On the other hand, for sample polymers ranging from ~10,000 to ~30,000,000 molecular weight, the shape of the eluting polymer peak was not observed to be substantially different at 0.5 ml/min. compared to 2.0 ml/min. eluent flow rate. However, this lack of observed flow rate dependence may be due to the high elongational strain rates in the column whereby the polymer may be stretched to the extent that other forces are negligible. To confirm this, the samples should be tested at flow rates on the order of 0.05 ml/min and less.

It is also important to understand what impact, if any, the solution concentration has on the elution position of the polymer. The solution viscosity as well as the linearity of the fluorescence response could impact on this effect. To investigate this influence, several dilutions of the same sample were analyzed and the resulting chromatograms compared. In general, the elution position can be influenced by the concentration of the sample. The difference in elution position between a 250 ppm and a 31 ppm of a 5$\overline{M}$ molecular weight polymer sample is measurable and corresponds to ~7 seconds of 0.005 R$_f$ units. No substantial change in elution position is observed however when comparing solution concentrations of less than 125 ppm of this sample solution. So, in general, the solution concentration should be kept below 125 ppm (or any maximum value determined by experiment for a given sample) and the possibility of elution position variation kept in mind when comparing samples of varying concentration.

An additional consideration, in anticipation of varying signal intensities due to varying composition, is the linearity of the detector signal. To evaluate this, one sample was analyzed following serial dilutions and the area of the peak associated with the polymer quantitated. Over the concentration range investigated, the response appears to be approximately linear.

To evaluate the influence of polymer composition on its elution position, a series of polyacrylamide polymers with the same molecular weight and varying degrees of hydrolysis were chromatographed using pH 4 eluent. The elution position relative to that of the marker remained relatively constant as the composition varied from 7.7 percent hydrolysis to 28.4 percent. These samples were prepared in an identical manner, including the concentrations of the polymer in the analyzed solutions. The variations in height of the chromatograms associated with polymer elution was a function of composition, as expected.

The calculated molecular weight distributions of the 28.4 percent and 7.7 percent samples are essentially identical. The calculated molecular weights for these samples are tabulated below.

TABLE II

| MW's for Composition Variation | |
|---|---|
| % Hydrolysis | $\overline{Mw}$ |
| 7.7 | 6.0$\overline{M}$ |
| 11.9 | 6.0$\overline{M}$ |
| 20.7 | 6.2$\overline{M}$ |
| 28.4 | 6.1M |

Example 5

Accuracy and Precision

The accuracy of this new method was evaluated by comparing the weight average molecular weight as determined by flow chromatography and by light scattering for several samples. Table III below summarizes this comparison.

TABLE III

| | $\overline{Mw}$ | |
|---|---|---|
| | Light Scattering | Invention |
| 1. | 5.3$\overline{M}$ | 5.0$\overline{M}$ |
| 2. | 2.9$\overline{M}$ | 2.0$\overline{M}$ |
| 3. | 5.5M | 5.1M |

The agreement between the molecular weights is within the precision of the two techniques for all three samples.

The precision of this chromatographic technique was determined by analyzing ten different tagged solutions of the same sample over a 2-day period. The results are tablulated below:

TABLE IV

| Precision Data | |
|---|---|
| Sample Number | $\overline{Mw}$ |
| 1 | 3.95$\overline{M}$ |
| 2 | 4.12$\overline{M}$ |
| 3 | 4.10$\overline{M}$ |
| 4 | 4.30$\overline{M}$ |
| 5 | 4.12$\overline{M}$ |
| 6 | 4.14$\overline{M}$ |
| 7 | 4.26$\overline{M}$ |
| 8 | 4.33$\overline{M}$ |
| 9 | 4.16$\overline{M}$ |
| 10 | 4.05$\overline{M}$ |

Mean 4.15$\overline{M}$
0.116$\overline{M}$ Std.
Relative Std. Dev. 2.8%
5.6% = RSD 2$\sigma$

EXAMPLE 6

Further Applications

The applications of the invention to various important water soluble polymers have been described in recent literature.

The use of the invention to characterize xanthan polysaccharide is described by Prud'homme et al, entitled "Molecular-Size Determination of Xanthan Polysaccharide," Carb. Res., 106, 225–233 (1982).

In addition, the graduate work of K. A. Larson, entitled "Separations of High Molecular Weight Water Soluble Polymers by Means of Hydrodynamic Chromatography," Department of Chemical Engineering, Princeton University (1983), documents and describes the chromatographic separations of partially hydrolyzed polyacrylamide polymers and DNA using the method of the invention.

These respective teachings are hereby fully incorporated in the present disclosure by reference.

What is claimed is:

1. A liquid chromatographic method for characterizing water soluble polymers by molecular weight and molecular weight distribution based on apparent size which comprises:

(a) adding to an aqueous eluent a sample of a detectable ultra-high molecular weight polymer in a solution concentration between the detectable limit and an upper limit below the concentration at which the elution of the polymer is detrimentally influenced by concentration, the sample added being dissolved in a primarily aqueous diluent not incompatible with the eluent, the added sample volume being not greater than that volume which would detrimentally influence the chromatography;

(b) passing the combined eluent and sample at a low flow rate which does not influence the elution position of the sample through a porous body composed of a packed bed of impenetrable particles whereby the apparent size fractions of the polymer sample are separated by flow chromatography;

(c) detecting the amount of the eluting apparent size fractions of the polymer species; and (d) using the data of step (c) to characterize the molecular weight and molecular weight distribution of the detected water soluble polymer.

2. The method of claim 1 used for characterizing the molecular weight and molecular weight distribution of polymer samples of about $\geq 2$ million weight average molecular weight ($\overline{M}_w$).

3. The method of claim 2 for characterizing a polyelectrolyte water soluble polymer using for the eluent, an aqueous solution the pH of which is controlled to convert or maintain the polymer of polyelectrolyte as a relatively nonionic species.

4. A liquid chromatographic method for characterizing water soluble polymers by molecular weight and molecular weight distribution based on apparent size which comprises:
   (a) tagging the polymer with a fluorescent group;
   (b) adding the polymer in aqueous diluent to an aqueous eluent;
   (c) passing the combined eluent and sample at a low flow rate which does not influence the elution position of the sample through a porous body composed of a packed bed of impenetrable particles whereby the apparent size fractions of the polymer sample are separated by flow chromatography;
   (d) detecting the amount of the eluting apparent size fractions of the polymer species based on fluorescence detection; and
   (e) using the data of step (d) to characterize the molecular weight and molecular weight distribution of the detected water soluble polymer.

5. The method of claim 4 used for characterizing the molecular weight and molecular weight distribution of polymer samples of about $\geq 2$ million weight average molecular weight ($\overline{M}_w$).

6. The method of claim 4 for characterizing a polyelectrolyte water soluble polymer using for the eluent, an aqueous solution the pH of which is controlled to convert or maintain the polymer polyelectrolyte as a relatively nonionic species.

* * * * *